US012808867B2

(12) United States Patent
Heikenfeld et al.

(10) Patent No.: US 12,808,867 B2
(45) Date of Patent: Nov. 24, 2026

(54) REDUCED ELECTRONIC SAMPLING OF APTAMER SENSORS

(71) Applicant: University of Cincinnati, Cincinnati, OH (US)

(72) Inventors: Jason Heikenfeld, Cincinnati, OH (US); Mark Friedel, Cincinnati, OH (US); Madeleine Debrosse, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 448 days.

(21) Appl. No.: 18/246,204

(22) PCT Filed: Sep. 24, 2021

(86) PCT No.: PCT/US2021/051914

§ 371 (c)(1),
(2) Date: Mar. 22, 2023

(87) PCT Pub. No.: WO2022/067011

PCT Pub. Date: Mar. 31, 2022

(65) Prior Publication Data

US 2023/0349894 A1 Nov. 2, 2023

Related U.S. Application Data

(60) Provisional application No. 63/215,605, filed on Jun. 28, 2021, provisional application No. 63/197,669, (Continued)

(51) Int. Cl.

*G01N 33/543* (2006.01)
*G01N 27/327* (2006.01)
*G01N 33/53* (2006.01)

(52) U.S. Cl.

CPC ..... *G01N 33/5438* (2013.01); *G01N 27/3277* (2013.01); *G01N 33/5306* (2013.01)

(58) Field of Classification Search

CPC ........... G01N 27/3277; G01N 33/5306; G01N 33/5308; G01N 33/5438; A61B 5/1451; A61B 5/14546; A61B 5/1468

See application file for complete search history.

(56) References Cited

U.S. PATENT DOCUMENTS

| | | | |
|---|---|---|---|
| 2008/0052024 A1 | 2/2008 | Tracy | |
| 2017/0059561 A1 | 3/2017 | Bhansali et al. | |

(Continued)

FOREIGN PATENT DOCUMENTS

| | | | | |
|---|---|---|---|---|
| CN | 109580745 A | 4/2019 | | |
| WO | WO-2017189122 A1 * | 11/2017 | ............... | A61B 5/01 |
| WO | WO-2019126620 A1 * | 6/2019 | ........... | G01N 33/743 |

OTHER PUBLICATIONS

PCT Office, International Search Report and Written Opinion issued in PCT/US2021/051914 dated Feb. 7, 2022.

(Continued)

*Primary Examiner* — C. Sun

(74) *Attorney, Agent, or Firm* — Wood Herron & Evans LLP

(57) ABSTRACT

Devices and methods for measuring an analyte. A sensing device 156 includes a sensor and a detection circuit operatively coupled to the sensor. The sensor includes a working electrode having an aptamer and an attached redox couple to electrochemically measure the analyte. The detection circuit is configured to perform a partial scan of the sensor, wherein the partial scan includes only a portion of a full scan. The working electrode may be one of a plurality of working electrodes, and the detection circuit may perform the partial scan on a different subset of the plurality of working electrodes on each of a plurality of measurement cycles.

(Continued)

Partial scans may include partial voltage scans, partial current scans, or partial frequency scans.

52 Claims, 7 Drawing Sheets

Related U.S. Application Data filed on Jun. 7, 2021, provisional application No. 63/150,675, filed on Feb. 18, 2021, provisional application No. 63/083,023, filed on Sep. 24, 2020.

(56) References Cited

U.S. PATENT DOCUMENTS

| | | | | |
|---|---|---|---|---|
| 2017/0299540 | A1* | 10/2017 | Wu | G01N 27/3272 |
| 2018/0074012 | A1* | 3/2018 | Wang | A61B 5/1459 |
| 2019/0200892 | A1* | 7/2019 | Beech | A61B 10/0064 |

OTHER PUBLICATIONS

European Patent Office, Supplementary European Search Report and D1a English machine translation of D1 CN109580745A as annexed to this communication, issued in European Application No. 21873496.0, dated Oct. 7, 2024.

Ni Shengnan et al., "Enhanced performance of an electrochemical aptasensor for real-time detection of vascular endothelial growth factor (VEGF) by nanofabrication and ratiometric measurement", Analytica Chimica Acta, Elsevier, Amsterdam, NL, vol. 1121, May 6, 2020, pp. 74-82, XP086160239, ISSN: 0003-2670, DOI: 10.1016/J.ACA.2020.05.003, retrieved on May 6, 2020.

European Patent Office, Examination Report issued in European Patent Application No. 21873496.0, dated Apr. 21, 2026, 6 pgs.

* cited by examiner

REDUCED ELECTRONIC SAMPLING OF APTAMER SENSORS

CROSS-REFERENCE TO RELATED APPLICATIONS

This application claims the benefit of Intl. App. No. PCT/US2021/051914, filed on Sep. 24, 2021 claiming the benefit of U.S. Patent Application Ser. No. 63/083,023, filed on Sep. 24, 2020, U.S. Patent Application Ser. No. 63/150,675, filed on Feb. 18, 2021, U.S. Patent Application Ser. No. 63/197,669, filed on Jun. 7, 2021, and U.S. Patent Application Ser. No. 63/215,605, filed on Jun. 28, 2021. The disclosures of each of the above applications are incorporated by reference herein in their entireties.

BACKGROUND OF THE INVENTION

This section is intended to introduce the reader to various aspects of the art that may be related to various aspects of the invention, which are described and/or claimed below. This discussion is believed to be helpful in providing the reader with background information to facilitate a better understanding of various aspects of the invention. Accordingly, it should be understood that these statements are to be read in this light, and not as admissions of prior art.

Aptamers are molecules that bind to a specific target molecule. Electrochemical aptamer sensors include an aptamer that specifically binds to an analyte of interest, and that is attached to an electrode. The aptamer has an attached redox active molecule (redox couple) which can transfer electrical charge to or from the electrode. When an analyte binds to the aptamer, the aptamer changes shape, changing the availability of a redox couple to transfer charge with the electrode. This results in a measurable change in electrical current that can be translated into a measure of the concentration of the analyte.

A major unresolved challenge for aptamers is extending the lifetime of the sensors, especially for applications where continuous operation is required, such as multiple measurements over time by the same device. Redox couples do not have infinite lifetime. Typically, the more they are used the more they degrade. The same is also true of the other materials/layers in the device, such as the blocking layer which reduces baseline current, the aptamer attachment to the electrode, the electrode material itself, and other materials/chemicals used in the sensor.

Thus, a need exists for improved device design and methods to reduce the electrochemical-induced degradations of aptamer sensor devices over time. Such an innovation could broadly advance the ability of aptamer sensors to be used in continuous or long duration sensing applications such as wearable or implantable sensors, and other types of applications.

SUMMARY OF THE INVENTION

Certain exemplary aspects of the invention are set forth below. It should be understood that these aspects are presented merely to provide the reader with a brief summary of certain forms the invention might take, and that these aspects are not intended to limit the scope of the invention.

Many of the drawbacks and limitations stated above can be resolved by creating novel and advanced interplays of chemicals, materials, sensors, electronics, microfluidics, algorithms, computing software, systems, and other features or designs, in a manner that affordably, effectively, conveniently, intelligently, or reliably brings sensing technology into proximity with sample fluids containing at least one analyte of interest to be measured.

In an embodiment of the invention, a sensing device for measuring an analyte is provided. The sensing device includes a sensor and a detection circuit. The sensor includes a working electrode with an aptamer and an attached redox couple to electrochemically measure the analyte. The detection circuit is operatively coupled to the sensor, and is configured to perform a partial scan of the sensor that only includes a portion of a full scan.

In an aspect of the invention, the working electrode may be one of a plurality of working electrodes configured to measure the analyte, and the detection circuit may be configured to perform the partial scan on a different subset of the plurality of working electrodes on each of at least two consecutive measurement cycles.

In another aspect of the invention, a plurality of subsets of the working electrodes may be scanned, and each subset may include at least three electrodes that are all scanned as part of a single measurement cycle.

In another aspect of the invention, the plurality of working electrodes may include at least 2, 3, 5, 10, 50, 100, 200, 500, or 1000 electrodes.

In another aspect of the invention, the partial scan may be one of a partial voltage scan, a partial current scan, or a partial frequency scan.

In another aspect of the invention, the partial scan may include providing a signal having a plurality of sampling periods to the sensor. Each sampling period may include a sampling duration, at least one set of consecutive sampling periods may be separated by a ramping period having a ramping duration, and the ramping duration may be at least 0.2%, 1.0%, 2.0%, 5.3%, 11.1%, 25.0%, 100%, 900%, or 1900% of the sampling duration.

In another aspect of the invention, the detection circuit may be further configured to partially scan the sensor a plurality of times at time intervals that are periodic, non-periodic, or random.

In another aspect of the invention, the partial scan may be one of a plurality of partial scans each associated with a measurement cycle, and the portion of the full scan provided by each partial scan may vary between measurement cycles.

In another aspect of the invention, the detection circuit may be further configured vary the portion of the full scan provided by each partial scan between measurement cycles.

In another aspect of the invention, each of the plurality of partial scans may have at least one of a starting voltage and an ending voltage, and the detection circuit may be further configured to shift at least one of the starting voltage and the ending voltage between measurement cycles.

In another aspect of the invention, the partial scan may include a first portion that generates a baseline sample range, and a second portion that generates a peak sample range.

In another aspect of the invention, the baseline sample range may only cover a portion of a baseline region, and the peak sample range may only cover a portion of a peak region generated by the full scan.

In another aspect of the invention, one or more of the peak region and the baseline region may be defined based on a slope of an output generated by the partial scan.

In another aspect of the invention, the full scan may have a voltage range of at least 0.4 volts, and the partial scan may have a voltage range of no more than 0.2 volts or 0.1 volts.

In another aspect of the invention, the first portion of the full scan range may be scanned less frequently than the second portion of the full scan range.

In another aspect of the invention, the second portion of the full scan range is scanned at least two times, five times, 10 times, 50 times, or 100 times as frequently as the first portion of the full scan range.

In another aspect of the invention, the partial scan may have a duty cycle that is less than 75%, 50%, 20%, 10%, 5%, 2%, or 1% of the full scan.

In another aspect of the invention, the partial scan may generate less than 0.75 times, 0.50 times, 0.20 times, 0.10 times, 0.05 times, 0.02 times, 0.01 times, or 0.001 times the total charge transfer generated by the full scan.

In another aspect of the invention, the partial scan may be a partial current scan having a current range that is <90%, <50%, <20%, <10%, <5% or <2% of the current range of a full current scan.

In another aspect of the invention, the partial scan may be a partial frequency scan having a frequency range that is <50%, <20%, <10%, <5%, or <2% of the frequency range of a full frequency scan.

In another embodiment of the invention, a method of measuring an analyte is provided. The method includes partially scanning the sensor that includes the working electrode having the aptamer and the attached redox couple to electrochemically measure the analyte, and partially scanning the sensor includes only providing a portion of the full scan to the sensor.

In an aspect of the invention, the working electrode may be one of the plurality of working electrodes configured to measure the analyte, and the method may further include performing the partial scan on the different subset of the plurality of working electrodes on each of the at least two consecutive measurement cycles.

In another aspect of the invention, the plurality of subsets of the working electrodes may be scanned, each subset may include at least three electrodes, and the method may further include scanning all of the at least three electrodes as part of a single measurement cycle.

In another aspect of the invention, partially scanning the sensor may include performing a partial voltage scan, a partial current scan, or a partial frequency scan.

In another aspect of the invention, partially scanning the sensor may include providing the signal having the plurality of sampling periods to the sensor. Each sampling period may have a sampling duration, at least one set of consecutive sampling periods of the plurality of sampling periods may be separated by the ramping period having the ramping duration, and the ramping duration may be at least 0.2%, 1.0%, 2.0%, 5.3%, 11.1%, 25.0%, 100%, 900%, or 1900% of the sampling duration.

In another aspect of the invention, the method may further include partially scanning the sensor a plurality of times, wherein the partial scans occur at time intervals that are periodic, non-periodic, or random.

In another aspect of the invention, each of the plurality of partial scans may be associated with a measurement cycle, and the portion of the full scan provided by each partial scan may vary between measurement cycles.

In another aspect of the invention, the partial scan may be a partial voltage scan including one or more portions of a voltage range associated with the full scan.

In another aspect of the invention, the partial voltage scan may include one or more voltage scans that cover a cumulative voltage range of less than 0.2 volts.

In another aspect of the invention, the method may further include partially scanning the sensor a plurality of times, wherein each of the plurality of partial scans is associated with a measurement cycle, and each partial scan has at least one of a starting voltage and an ending voltage that is shifted in voltage over time between measurement cycles.

In another aspect of the invention, the one or more portions of the voltage range may include at least one baseline partial scan of the baseline region, and at least one peak partial scan associated with the full scan.

In another aspect of the invention, the method may further include partially scanning the sensor a plurality of times to generate a plurality of partial scans. A first portion of the plurality of partial scans may include at least one baseline partial scan, a second portion of the plurality of partial scans may include at least one peak partial scan, and the number of partial scans in the second portion of the plurality of partial scans may be greater than the number of partial scans in the first portion of the plurality of partial scans.

In another aspect of the invention, an electrical charge may be transferred by the partial scan that generates less than half of the electrical charge transfer associated with the full scan.

In another aspect of the invention, partially scanning the sensor may include performing a partial current scan, and the partial current scan may have a duration that is less than 90% of the amount of time a full current scan would take to transfer 98% of the total charge transferred by the full scan.

In another aspect of the invention, partially scanning the sensor may include performing a partial frequency scan, and the partial frequency scan may include less than 50% of a full scanning frequency range.

In another aspect of the invention, the partial frequency scan may include at least one peak frequency for changes in signal gain.

In another aspect of the invention, the partial frequency scan may include at least one peak frequency with no signal gain.

In another aspect of the invention, partially scanning the sensor may include scanning the first portion of the full scan that generates the baseline sample range, and scanning the second portion of the full scan that generates the peak sample range.

In another embodiment of the invention, another sensing device for measuring the analyte is provided. The sensing device includes the sensor and the detection device operatively coupled to the sensor. The sensor includes a plurality of working electrodes each having an aptamer and an attached redox couple to electrochemically measure the analyte. The detection circuit is configured to perform a scan of the sensor by scanning a different subset of the plurality of working electrodes on each of at least two consecutive measurement cycles.

In another embodiment of the invention, another method of measuring an analyte is provided. The method includes scanning a first subset of the working electrodes during a first measurement cycle, and scanning a second subset of the working electrodes during a second measurement cycle that follows the first measurement cycle, wherein the first subset is different from the second subset.

BRIEF DESCRIPTION OF THE DRAWINGS

The objects and advantages of the disclosed invention will be further appreciated in light of the following detailed descriptions and drawings in which.

DEFINITIONS

Figure 1A:
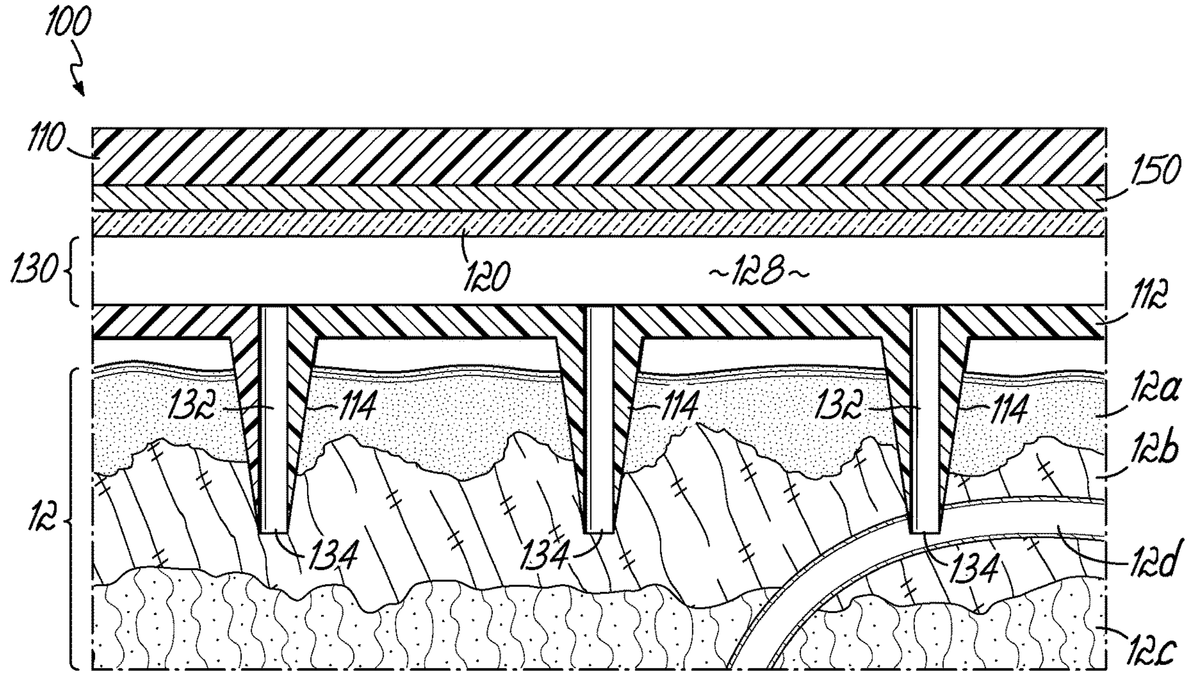
FIGS. 1A and 1B are cross-sectional views of an exemplary sensing device in accordance with an embodiment of the invention.

As used herein, the term "about," when referring to a value or to an amount of mass, weight, time, volume, pH, size, concentration, or percentage, is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and operate the disclosed devices.

As used herein, the term "aptamer" means a molecule that undergoes a conformation change as an analyte binds to the molecule, and which satisfies the general operating principles of the sensing methods and devices as described herein. Such molecules are, e.g., natural or modified DNA, RNA, or XNA oligonucleotide sequences, spiegelmers, peptide aptamers, and affimers. Modifications may include substituting unnatural nucleic acid bases for natural bases within the aptamer sequence, replacing natural sequences with unnatural sequences, or other suitable modifications that improve sensor function. Typically, aptamers used in electrochemical sensors are tagged with a redox molecule such as methylene blue.

The devices and methods described herein encompass the use of sensors. A sensor, as used herein, is a device that is capable of measuring the concentration of a target analyte in solution. As used herein, an "analyte" may be any inorganic or organic molecule, for example: a small molecule drug, a metabolite, a hormone, a peptide, a protein, a carbohydrate, a nucleic acid, or any other composition of matter. The target analyte may comprise a drug. The drug may be of any type, for example, including drugs for the treatment of cardiac system, the treatment of the central nervous system, that modulate the immune system, that modulate the endocrine system, an antibiotic agent, a chemotherapeutic drug, or an illicit drug. The target analyte may comprise a naturally-occurring factor, for example a hormone, metabolite, growth factor, neurotransmitter, etc. The target analyte may comprise any other species of interest, for example, species such as pathogens (including pathogen induced or derived factors), nutrients, and pollutants, etc.

As used herein, the term "duty cycle" refers to the portion of a scanning signal (e.g., a voltage signal that is varied within a voltage range, a current signal that is varied within a current range, or a frequency that is varied within a frequency range) that is applied during operation of a sensor as a percentage of the "full scan", which is the total available voltage, current, and/or frequency range typically used for operation of the sensor.

As used herein, the term "continuous sensing" may be satisfied by the device recording a plurality of readings over a period of time during which the sensing occurs. Thus, even a point-of-care testing device which provides a single data point can be considered a continuous sensing device if, for example, the test has a 15 minute duration, and the testing device operates by taking multiple data points over 15 minutes and averaging them to provide a single data measure.

DETAILED DESCRIPTION OF THE INVENTION

One or more specific embodiments of the invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Certain embodiments of the disclosed invention show sensors as simple individual elements. It is understood that many sensors require two or more electrodes, reference electrodes, or additional supporting technology or features that, for purposes of clarity, are not necessarily described herein. Sensors measure a characteristic of an analyte. Sensors are preferably electrical in nature, but may also include optical, chemical, mechanical, or other known sensing mechanisms. Sensors can be in duplicate, triplicate, or more, to provide improved data and readings. Sensors may provide continuous or discrete data and/or readings. Certain embodiments of the disclosed invention may show certain sub-components of sensing devices, but may omit additional sub-components needed for use of the device in various applications that are known, e.g., a battery, antenna, adhesive. These omissions may be for purposes of brevity and to focus on certain inventive aspects of the disclosed embodiments of the invention. All ranges of parameters disclosed herein include the endpoints of the ranges.

With reference to FIG. 1A, and in accordance with an embodiment of the invention, an exemplary sensing device 100 is shown placed partially in-vivo into skin 12 including an epidermis 12*a*, a dermis 12*b*, and a subcutaneous or hypodermis 12*c*. The sensing device 100 includes a non-conductive substrate 110 (e.g., a polymer), a microneedle assembly 112, a sensing layer 120, and an electrode layer 150 that couples the sensing layer 120 to the substrate 110. A portion of the sensing device 100 receives a fluid, e.g., an invasive biofluid such as an interstitial fluid from the dermis 12*b* and/or blood from a capillary 12*d*. Access to the fluid may be provided, for example, by the microneedle assembly 112. The microneedle assembly 112 may be formed of metal, polymer, semiconductor, glass, or other suitable material, and include a plurality of microneedles 114. Each microneedle 114 may include a lumen 132 having an inlet 134 that provides access to the fluid.

The sensing device 100 may further include a sample volume 128 comprising a space 130 defined between the microneedle assembly 112 and the sensing layer 120, and the lumens 132. The sensing layer 120 and electrode layer 150 may form a working electrode of the sensing device 100. The sample volume 128 may be filled with a microfluidic component such as capillary channels, a hydrogel, or other suitable material, that operatively couples the fluid to the sensing layer 120. Thus, a diffusion and/or adjective flow pathway may be provided between the fluid to be sensed and the sensing layer 120. This pathway may begin at the inlets 134 to the microneedles 114 and reach the sensing layer 120. Alternative arrangements and materials may also be possible, such as using a single needle, hydrogel polymer microneedles, or other suitable means to couple the fluid to one or more sensors. Thus, embodiments of the invention are not limited to the depicted sensing device 100. In addition, a portion of sensing device 100, or even the entire sensing device 100, could be implanted into the body and perform similarly as described herein. For example, the electrode layer 150 and sensing layer 120 may be implanted inside the body on the end of an indwelling needle like those used in continuous glucose monitors.

With further reference to FIG. 1A, the sensing layer 120 may be affinity-based, and may include, for example, one or more aptamers. The aptamers may be selective in reversible binding to an analyte, thiol bonded to the electrode layer 150, and used to sense an analyte by means of electrochemical detection. The electrode layer 150 may include a suitable conductive material, such as gold, carbon, or other suitable electrically conducting material. The sensing device 100 may be electrical in nature, and may utilize an attached redox couple to transduce the electrochemical signal. The sensing device 100 may also measure changes in impedance between the working electrode and the fluid being sensed.

Figure 1B:
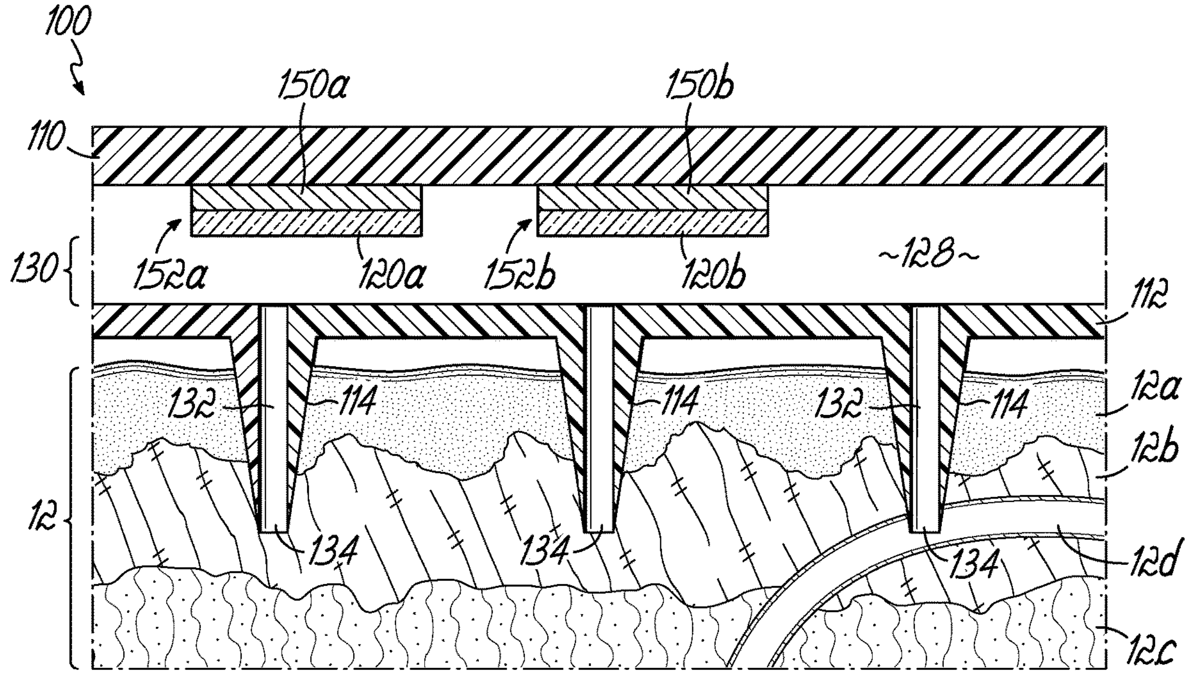

Although the exemplary embodiments depicted by FIGS. 1A and 1B use microneedles to access an interstitial fluid, it should be understood that embodiments of the invention are not so limited. Thus, it should be further understood that the principles of the invention may apply to additional applications of aptamer sensors, such as sensors for monitoring environmental pollutants, for food processing safety, for implanted sensors, or for any other suitable applications and devices.

With reference to FIG. 1B, where like numerals refer to like features in the previous figures, the sensing device 100 may include a plurality of working electrodes 152 for sensing one or more analytes. By way of example, the plurality of working electrodes 152 may include one or more working electrodes 152*a* having an electrode layer 150*a* and a sensing layer 120*a* configured to detect a drug such as cocaine, and another one or more working electrodes 152*b* having an electrode layer 150*b* and a sensing layer 120*b* configured to detect a metabolite, such as phenyalanine. In an alternative embodiment, both sets of one or more working electrodes 152*a*, 152*b* may be configured to detect a single analyte, such as doxorubicin. Thus, the sensing device 100 may include one or more sensors for each of one or more analytes.

Figure 1C:
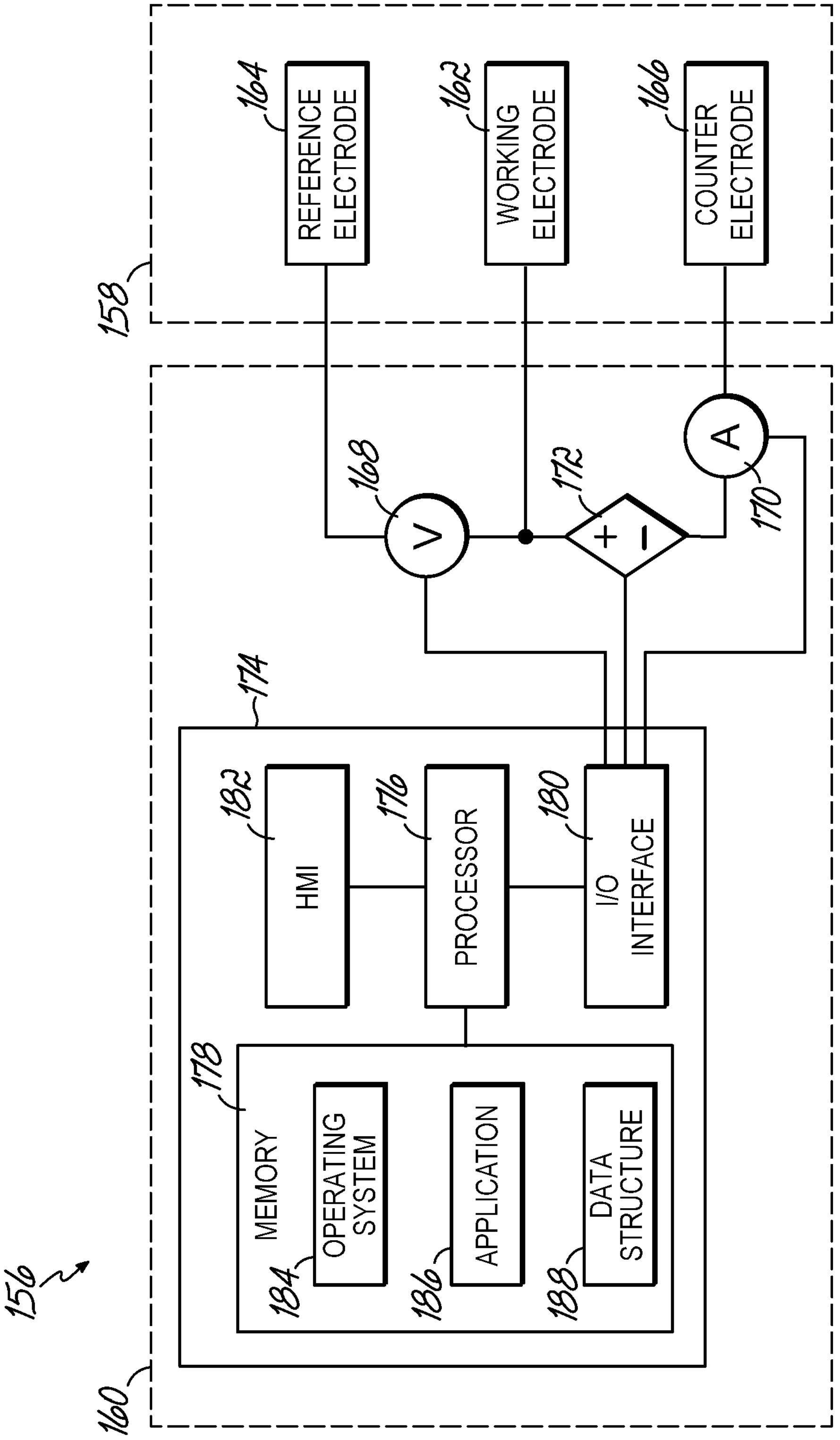
FIG. 1C is a schematic view of an exemplary sensing device in accordance with another embodiment of the invention.

FIG. 1C depicts an exemplary sensing device 156 that includes a sensor 158 and a detection circuit 160. The sensor 158 includes one or more electrodes, e.g., a working electrode 162, a reference electrode 164, and a counter electrode 166. The detection circuit 160 may include a voltage sensor 168, a current sensor 170, a voltage source 172, and a controller 174. The voltage sensor 168 may be operatively coupled to the working and reference electrodes 162, 164 to measure a voltage therebetween. The current sensor 170 may be operatively coupled to the working and counter electrodes 162, 166 to measure a current flowing therebetween. The voltage source 172 may be operatively coupled to the working and counter electrodes 162, 166, and may be controlled by the controller 174 to selectively apply voltages between the working and counter electrodes 162, 166.

The controller 174 may comprise a computing device that includes a processor 176, a memory 178, an input/output (I/O) interface 180, and a Human Machine Interface (HMI) 182. The processor 176 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions stored in memory 178. Memory 178 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or data storage devices such as a hard drive, optical drive, tape drive, volatile or non-volatile solid state device, or any other device capable of storing data.

The processor 176 may operate under the control of an operating system 184 that resides in memory 178. The operating system 184 may manage computer resources so that computer program code embodied as one or more computer software applications 186 residing in memory 178 can have instructions executed by the processor 176. One or more data structures 188 may also reside in memory 178, and may be used by the processor 176, operating system 184, or application 186 to store or manipulate data.

The I/O interface 180 may provide a machine interface that operatively couples the processor 176 to other devices and systems, such as the voltage sensor 168, current sensor 170, and voltage source 172. The application 186 may thereby work cooperatively with the other devices and systems by communicating via the I/O interface 180 to provide the various features, functions, applications, processes, or modules comprising embodiments of the invention.

The HMI 182 may be operatively coupled to the processor 176 of controller 174 to allow a user to interact directly with the sensing device 156. The HMI 182 may include video or alphanumeric displays, a touch screen, a speaker, and any other suitable audio and visual indicators capable of providing data to the user. The HMI 182 may also include input devices and controls such as an alphanumeric keyboard, a pointing device, keypads, pushbuttons, control knobs, microphones, etc., capable of accepting commands or input from the user and transmitting the entered input to the processor 176.

Referring again to FIG. 1B, the sensing device 100 may use a plurality of working electrodes 152 each configured to detect the same analyte, but the sensors may not always be used simultaneously. That is, different working electrodes or subsets including one or more of a plurality of working electrodes may be selectively used at different times to detect the same analyte, thereby extending the working lifetime of the working electrodes 152. To prolong the use of the sensing device 100, an embodiment of the invention may use a sensing device comprising a plurality of working electrodes. In operation, a subset of the plurality of working electrodes may be used for multiple sequential scans until one or more electrodes in the subset of electrodes fails. In response to detecting this failure, the sensing device may switch to another functional electrode for subsequent scans. When that electrode fails, the process may be repeated. Each subset of electrodes may consist of an individual electrode, or any number of electrodes that is less than the total number of electrodes in the plurality of electrodes. Subsets of the plurality of electrodes may be overlapping or non-overlapping. Overlapping subsets include one or more electrodes that are also members of one or more other subsets with which they overlap, while non-overlapping subsets do not include any electrodes that are members of more than one of the non-overlapping subsets.

In an alternative embodiment, each sequential scan may be conducted on a different electrode or subset of electrodes until they have all been used, at which point the process repeats. Sequential scanning may be advantageous because electrodes can degrade and change over time due to other factors. Thus, sequential scanning may allow for a more easily interpretable continuum of data to be recorded over time as compared to use-to-failure embodiments. In any case, sequential scans may be performed in a periodic, a non-periodic, or random manner. For example, measurement cycles may occur at predetermined intervals of time, at intervals of time having a predetermined pattern, or at random intervals of time.

In an exemplary embodiment, an electrochemical aptamer-based (EAB) sensing device may use the same type of reference and counter electrodes for all the aptamer sensor electrodes. By way of example, at least 2, 3, 5, 10, 50, 100, 200, 500, or 1000 sensor electrodes may be used in one EAB sensing device, although embodiments of the invention are not limited to any particular number of sensor electrodes. For example, if 200 electrodes are used, each individual electrode may experience 0.005 the electrochemical fatigue during a particular use period as compared to a single electrode having to support all the measurements during that use period. This method may effectively reduce the duty cycle that any one electrode must experience while sustaining the frequency of measurements needed to support continuous sensing. For example, a drug measurement that must be taken every minute for three days would require 4320 measurements in total over the measurement period. A single sensor would have to support 4320 measurements, whereas 10 sensors as taught herein would each individually only have to support around 432 such measurements. In some cases, measuring multiple electrodes simultaneously or near in time to each other can reduce measurement error, e.g., by measuring multiple sensors for each datapoint.

Embodiments of the invention may permit a subset of sensors (e.g., a subset of electrodes or sensors) to be measured at any given time to reduce measurement error or to improve the statistical validity of a measurement. The subset of sensors measured may change over time to increase the measurement lifetime of the sensing device unit. As a non-limiting example, one sensor at a time can measure a drug while the concentration of the drug is within its safe therapeutic window. However, during dosing of the drug and rapid uptake in the body, the drug concentration may be higher initially. To achieve more accurate data, three or more sensors could be used to represent each datapoint. Alternatively, one sensor could be used more often (e.g., every 5 minutes right after drug ingestion vs. every 30 minutes or every 3 hours after drug ingestion). As a result, the amount of sampling of the sensor may be reduced, thereby improving its longevity.

Figure 2A:
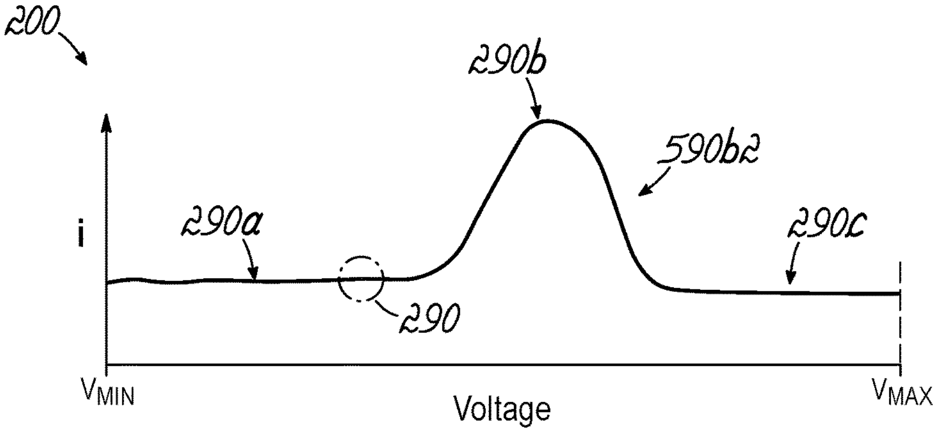
FIGS. 2A-2C are graphical views illustrating sampling methods to reduce the electrochemical sampling imparted on an electrochemical aptamer based sensor that uses voltage scans.

FIG. 2A depicts a graph 200 in accordance with another exemplary embodiment of the invention. The graph 200 includes a plot 290 of current verses voltage for a full scan (e.g., $V_{MIN}$ to $V_{MAX}$)) of an exemplary sensor. In a typical operational environment, $V_{MIN}$ may be about 0 volts, and $V_{MAX}$ may be about 0.4 volts. Aptamers with redox tags on working electrodes are typically measured using a form of pulse voltammetry, such as Square Wave Voltammetry (SWV), although other methods may also be used. In SWV, a voltage (V) that causes a corresponding current output (I) is swept (as shown and described in more detail below in reference to FIG. 5A). The current results due to the redox couple transferring electrical charge to/from the working electrode. Whether SWV or another method is used to scan the sensor, a voltage scan range is typically used that provides a "full scan". A full scan normally includes a baseline region 290*a*, 290*c* having a baseline current, and at least one redox peak region 290*b*. Measuring the baseline current generated in the baseline region 290*a*, 290*c* may improve accuracy as the magnitude of the current in the peak region 290*b* can shift over time as the baseline current in the baseline region 290*a*, 290*c* increases or decreases. This shift in magnitude may be due to fouling, loss of the blocking layer, or other factors. Furthermore, the peak region 290*b* can also shift in voltage position over time due to effects such as changes in pH, fouling, analyte binding, salinity, reference electrode degradation, and other factors. Therefore, the voltage position of the peak region 290*b* may benefit from tracking the peak position over time.

Figure 2B:
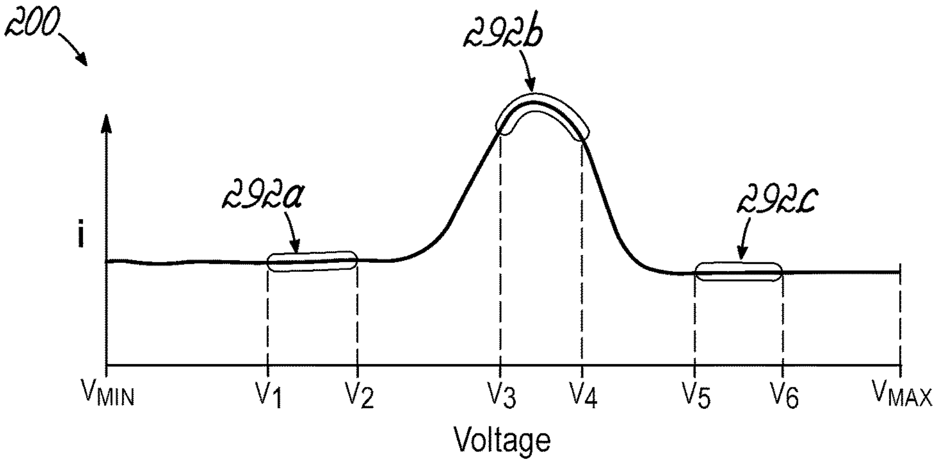

With reference to FIG. 2B, a partial scan may be substituted for a full scan to reduce electrochemical degradation of the electrochemical aptamer sensor. The size of the voltage scan range can be influenced by a number of SWV parameters including, but not limited to, the current range to be measured, the step frequency, and step width (which is generally in volts). However, during traditional measurements, most of the voltage scan range probed may not be necessary to determine EAB sensor response. Because electrical currents and fields experienced by the working electrode can degrade one or more materials that form the aptamer sensor, full scans may cause sensor degradation with each and every measurement cycle as compared to partial scans. Thus, eliminating irrelevant or lower value measurement regions can reduce active sensor time, and increase sensor longevity.

In a research environment, all regions of the voltage scan range may be irrelevant because a full scan is needed to confirm the data has a proper redox peak, and because research environments do not need sensors that last for days to run experiments. In commercial applications, it is possible to monitor only the voltage sub-regions that need to be measured to continuously confirm a high quality signal. Thus, in commercial settings, partial scans may allow longer duration operation, thereby cutting costs by replacing sensors less frequently, which is also desired commercially. This increased duration may be particularly beneficial, as once nuclease degradation of the aptamers is removed by membrane protection and/or mutating the aptamer sequence, and severe sensor surface fouling is prevented, the electrochemical degradation during sampling can be the dominant degradation mechanism.

Figure 2C:
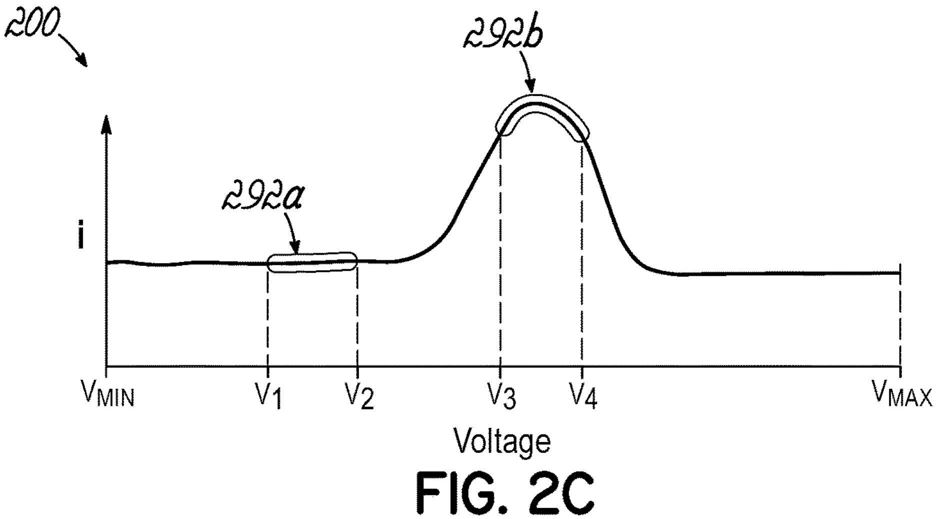

FIG. 2B depicts a partial scan that includes portions of the voltage scan range which produce a plurality of current baseline sample ranges 292*a*, 292*c* (e.g., two current sample ranges associated with scanning voltage sub-ranges $V_1$-$V_2$ and $V_5$-$V_6$, respectively) and a current peak sample range 292*b* ($V_3$-$V_4$). As shown in FIG. 2C, measurements may also be made using only two of these portions of the full scan, e.g., one current baseline sample range 292*a* and the current peak sample range 292*b*. A partial scan may include only one current sample range, or any number of current sample ranges so long as the scan voltage sub-ranges used to generate the current sample ranges do not collectively comprise the full voltage scan range. FIG. 2A may represent a forward voltammogram scan, a backward voltammogram scan, a net voltammogram scan (e.g., forward and backward data are combined as illustrated later in FIG. 5A), a portion of a cyclic voltammogram, or some other scan, with the main illustrative point of FIG. 2A being that there exists a redox peak region and a baseline region, and that both provide information needed to evaluate signals from an aptamer based sensor.

With further reference to FIGS. 2B and 2C, a variety of methods may be used to reduce the effective duty cycle of voltage and current scans used to obtain a sensor measurement. For example, a baseline partial scan that produces current sample ranges 292*a* or 292*c* could be performed less often than a peak partial scan that produces current sample range 292*b*. Less frequent baseline partial scans may be acceptable because the baseline signal changes slowly and/or the baseline changes can be predictable. In contrast, the peak signal can change more rapidly and is typically less predictable because it reflects changes in the concentration of the analyte. For example, 292*b* could be measured every five minutes whereas 292*a* could be measured only every 30 minutes. For example, a measurement of the current peak sample range 292*b* could be performed at least two times, five times, 10 times, 50 times, or 100 times more often than a measurement of the current baseline sample ranges 292*a* or 292*c*. Such an approach could be particularly beneficial if the redox peak region 290*b* or 292*b* lies at a position which also has little or minimal degradation of the electrode, which may depend on the electrode material (Au, carbon, etc.).

Current baseline sample range 292*a* and/or current baseline sample range 292*c* may also be measured in multiple ways. For example, by using an additional electrode with no redox couples, by varying the frequency of interrogation of the measurement such that the current peak sample range 292*b* is comparable to the current baseline sample range that would exist at that voltage where the peak 292*b* exists. This variable frequency technique may take advantage of the fact EAB sensors typically have a zero signal gain frequency. These examples show that the terms baseline and peak should not be narrowly limited to their exact representation shown in FIGS. 2A-2C, and should be more broadly interpreted so long as they achieve the desired outcome for embodiments of the invention, which is reduced sampling of an aptamer sensor.

The maximum voltage $V_{MAX}$ applied to the sensor may also be reduced to provide a partial voltage scan and improved lifetime. For example, the voltage could be scanned from $V_{MIN}$ or $V_1$ to $V_4$ in order to limit the maximum voltage applied to the device and avoid voltages that include $V_5$ to $V_6$ and beyond. Therefore, the controller 174 may cause the voltage source 172 to only scan up to the point where the peak current 292 is properly measured (e.g., up to $V_4$) and not beyond. For example, a conventional scan will typically cover ~0.4 volts or more, and with embodiments of the invention, the scan length could be less than 0.2 volts or less than 0.1 volts to capture adequate baseline and peak. Even if the baseline is partially affected by the peak, the baseline can also be predicted from the partial shape of the peak since the peak is super-imposed on the baseline.

Generally, a full voltage scan would include sufficient scanning before and after the redox peak voltage to capture baseline current values on both sides of the peak. Thus, a full voltage scan may be defined as a scan covering a voltage range that includes the redox peak and a sufficient amount of adjacent baseline where the additional current contribution from redox of the redox tag is less than 3% of the current contributed by redox of the redox tag at the peak redox tag current across the voltage range. Exemplary voltage scans that may be considered as partial scans include voltage scans having a voltage duty cycle that is less than 75%, 50%, 20%, 10%, 5%, 2%, or 1% of the full voltage scan as defined above.

A non-limiting example of a full voltage scan in one direction (negative or positive) or a net voltammogram for methylene blue is approximately 0 to −0.5 volts. In this example, the redox peak may occur from approximately −0.2 to −0.3 volts at near neutral pH and with an Ag/AgCl reference electrode. As another example, consider ferricyanide with a peak near −0.1 to −0.2 volts, or consider Nile blue with a wider redox peak spanning −0.3 to −0.5 volts.

Another way to distinguish partial voltage scans from full voltage scans may be by the total charge used to measure the sensor. For example, if a full voltage scan generates a total charge transfer of X coulombs, a voltage scan that generates less than 0.75 times, 0.50 times, 0.20 times, 0.10 times, 0.05 times, 0.02 times, 0.01 times, or even 0.001 times the total charge transfer X may be considered as a partial voltage scan. Alternately, the total charge transfer of the redox peak could be X, which may be provided by integrating the area under the redox peak curve. In this case, a voltage scan that generates less than 0.75 times, 0.50 times, 0.20 times, 0.10 times, 0.05 times, 0.02 times, 0.01 times, or even 0.001 times the total charge transfer X associated with the redox peak could be considered as a partial voltage scan.

Measurement variables such as electrochemical aptamer sensor composition, reference electrode characteristics (e.g., surface area), and environmental factors such as pH can change the position of key factors, such as current versus voltage values. Therefore, a methodology for determining key features and prediction their positions may be used to properly query sensors while minimizing oversampling that takes into account these variables. To this end, embodiments of the invention may monitor the position of baseline and peak currents over time, and adjust the partial scanning voltages such that they stay optimally aligned with these positions. For example, periodically or as needed, a full voltage scan could be performed to reveal the positions of all peaks and baselines. For example, a rising slope, apex of the peak with zero slope or alternately positive slope followed by negative slope, or falling slope of the peak could be measured to monitor peak position. Slope values may vary in a predictable way based on measurement variables. Thus, the slope values used to define boundaries between peak regions and baseline regions of a scan may be set based on the particular measurement environment being used.

Figure 2D:
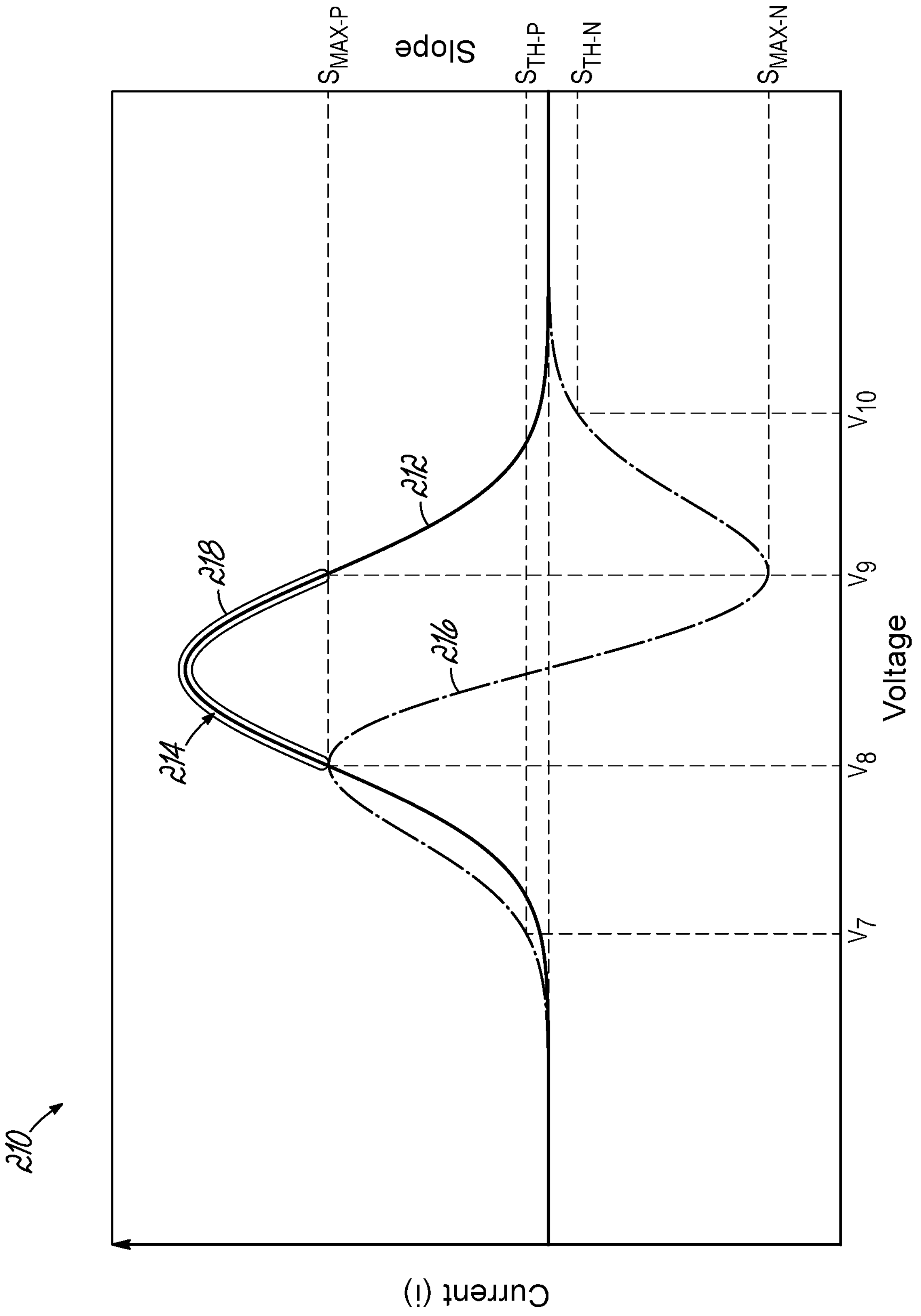
FIG. 2D is a graphical view illustrating exemplary ways of defining peak and baseline regions of a voltage scan.

By way of example, FIG. 2D depicts a graph 210 including an exemplary plot 212 of a voltage scan having a peak region 214, and a plot 216 showing the slope (di/dv) of the voltage scan. The slope of the voltage scan may have a peak positive slope $S_{MAX-P}$ at voltage $V_8$, and a peak negative slope $S_{MAX-N}$ at voltage $V_9$. A peak sample range 218 may be defined, for example, as a portion of the peak region 214 between the peak positive slope $S_{MAX-P}$ and the peak negative slope $S_{MAX-N}$. In an alternative embodiment, the peak sample range 218 may be defined as a percentage of the voltage range $V_8$-$V_9$ defined by the peak positive and negative slopes $S_{MAX-P}$, $S_{MAX-N}$, e.g., as 75%, 50%, 20%, 10%, 5%, 2%, or 1% of the voltage range $V_8$-$V_9$. In another alternative embodiment, the peak sample range 218 may be defined as a portion of the voltage scan between a voltage $V_7$ at which the scan slope exceeds a positive slope threshold $S_{TH-P}$, and a voltage $V_{10}$ at which the scan slope exceeds a negative slope threshold $S_{TH-N}$. Each of the positive and negative slope thresholds $S_{TH-P}$, $S_{TH-N}$ may be defined, for example, as a percentage of the peak positive slope $S_{MAX-P}$ and/or peak negative slope $S_{MAX-N}$, e.g., 75%, 50%, 20%, 10%, 5%, 2%, or 1% of the peak positive or peak negative slopes $S_{TH-P}$, $S_{TH-N}$. The edges of the peak region 214 may also be defined based on the slope of the voltage scan passing through one or more slope thresholds, and the peak position may be defined as the scan voltage at which the slope of the voltage scan passes through zero between the peak positive and peak negative slopes $S_{MAX-P}$, $S_{MAX-N}$. In an alternative embodiment, the edges of the peak region 214 may be defined as being a predetermined voltage below the positive slope threshold $S_{TH-P}$ and at a predetermined voltage above the negative slope threshold $S_{TH-N}$. In yet another embodiment, the peak edges and location may be defined by voltages at which the current i of the voltage scan exceeds one or more thresholds.

The voltage scans may also shift predictably. To accommodate these shifts, an embodiment of the invention may automatically adjust the positions of the voltage scans over time without measurement at all, or only with intermittent measurements. For example, if the peak shifted by +2.4 mV every 60 minutes, the peak could be measured every hour to confirm the rate of peak shifting, and if the sensor was measured every 10 minutes, the peak voltage that is scanned would be automatically shifted by +0.4 mV for each 10 minutes.

Figure 3A:
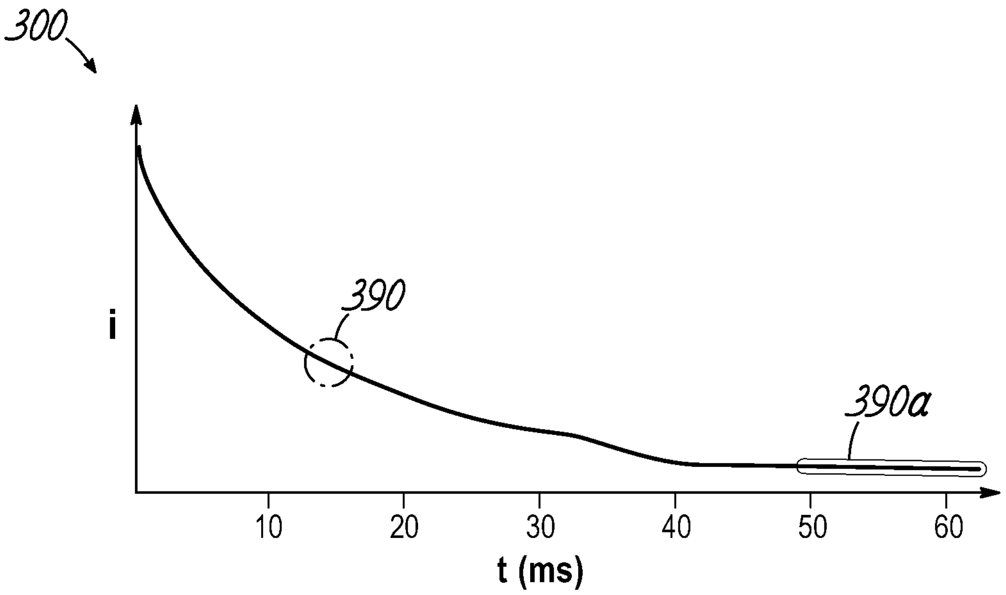
FIGS. 3A and 3B are graphical views illustrating sampling methods to reduce the electrochemical sampling imparted on an electrochemical aptamer based sensor that uses current scans.

Scanning signals applied to the sensor of a sensing device may include voltage scans (as described above), current scans, frequency scans, and combinations of voltage, current, and frequency scans. FIG. 3A depicts a graph 300 including a plot 390 of a partial current scan. The partial current scan represented by plot 390 may be configured to reduce electrochemical degradation of the electrochemical aptamer sensor. The scan in FIG. 3A may be a current scan for an aptamer sensor in which the lifetime of the redox current decay is independent of the current amplitude. That is, the redox current decay is insensitive to variations in the number of aptamer probes on the electrode. This characteristic may allow such sensors to be more calibration free and less susceptible to drift. After double layer charging effects (typically less than 1 ms), the rest of the decay curve changes by several fold (more than an order of magnitude) due to a depletion of the number of redox reporters which still have not transferred an electron to/from the electrode. Such scanning is similar to chronocoulometric measurement, which measures total charge, not current.

Figure 3B:
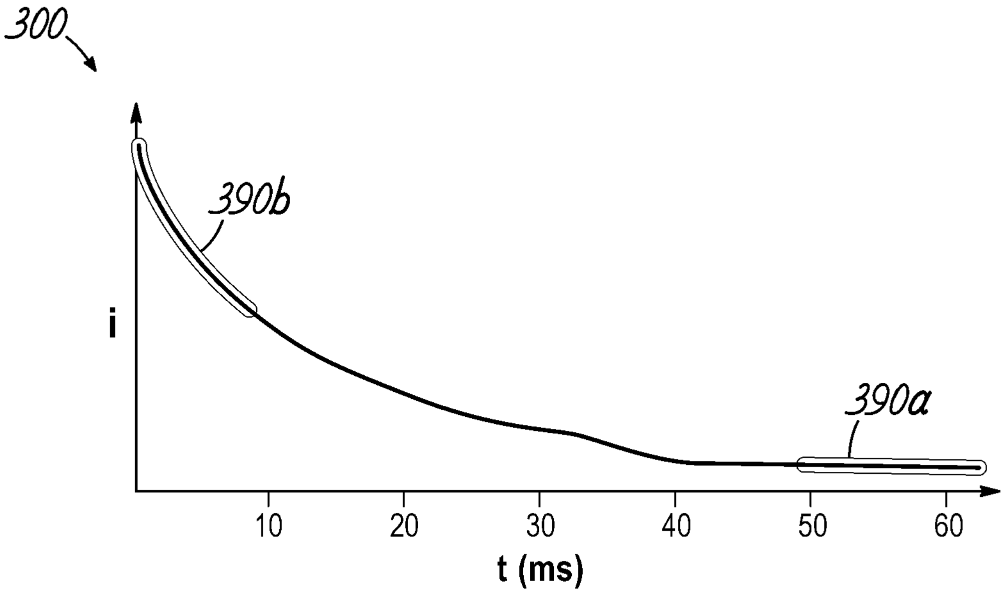

Thus, embodiments of the invention may also be applied to chronocoulometric measurements. As defined herein, a full current scan may start at t=0 and end at baseline when greater than a threshold percentage (e.g., 98%) of the total charge transfer from the redox couples has occurred, or when greater than the threshold percentage of the charged to be transferred has been transferred, respectively. The threshold percentage for chronoamperometry is illustrated in FIG. 3A as reaching current baseline sample range 390*a*. FIG. 3A is a single example only as the time to reach current baseline sample range 390*a* can be <10 ms to >100 ms depending on redox reporter and its distance from and kinetics related to the electrode. As shown in FIG. 3B, a partial current scan current sample range 390*b* is utilized to reduce total current and therefore degradation of the sensor. It can take a long time for a sensor to reach baseline in chronoamperometry or chronocoulometry, which imparts additional degradation of a sensor electrode without much added benefit in terms of the quality of the sensor measurement. Therefore, the partial current scan can be <90%, <50%, <20%, <10%, <5% or <2% of the full current scan.

Figure 4A:
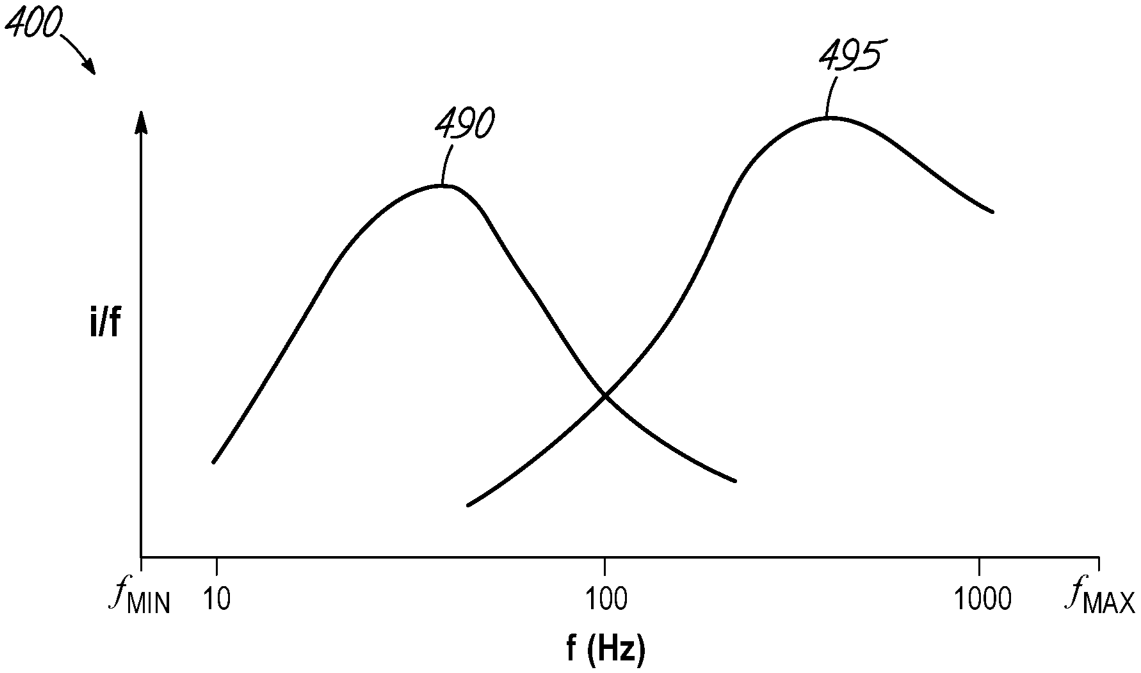
FIGS. 4A and 4B are graphical views illustrating sampling methods to reduce the electrochemical sampling imparted on an electrochemical aptamer based sensor that uses frequency scans.

FIG. 4A depicts a graph 400 including plots 490, 495 of current verse frequency. A partial frequency scan may be performed to reduce sampling of the sensor and therefore reduce sensor degradation. Aptamer sensors are normally optimized by scanning both voltage and frequency. For many aptamers, there are two or more frequencies that provide maximal signal change, one frequency being without the target analyte as shown by plot 490, and one being with the target analyte, as shown by plot 495. The intersection of plots 490, 495 identify a zero-signal gain region. Furthermore, an aptamer sensor may be optimized for a frequency that provides maximum signal gain for only a single "signal on" or "signal off" configuration, or both frequencies can be used to help preserve calibration or performance of the sensor measurement.

By way of explaining this frequency effect more deeply, the application of a voltage bias to the sensor interface generates electrokinetic, faradaic, mass, and charge transport phenomena that affect the output of these sensors. First, the sample electrolyte responds to voltage perturbations by dynamically aligning to their electrical fields. This effect generates double-layer charging/discharging currents in electrochemical measurements. Moreover, the voltage perturbation may cause field-induced movement actuation of the negatively charged aptamer backbone. This effect perturbs the frequency of electron transfer which, in turn, affects sensor signaling currents. Beyond field-induced modulation of the electrolyte and aptamer strands, mass transport of the redox reporter to the electrode also affects electron transfer. Furthermore, aptamer secondary structures and the thickness of the electrode-blocking monolayer and any foulants on that surface affect the currents measured, as do the standard electron transfer rate of the redox reporter and the rates of receptor-target ligand association/dissociation. All of these factors can influence the ideal measurement frequency of aptamer sensors.

Figure 4B:
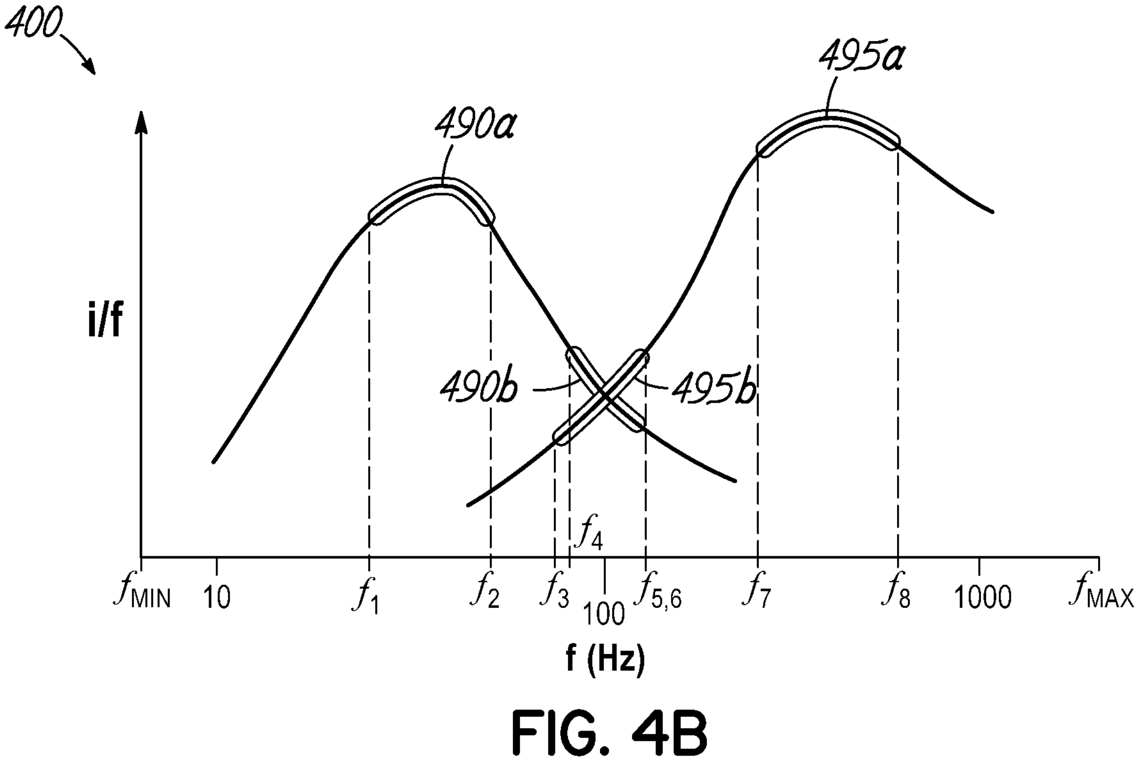

Because the frequencies that provide maximal signal change can change during sensor use, a subset of frequencies may be scanned periodically to identify any frequency dependent changes. FIG. 4B depicts the graph 400 in FIG. 4B with current sample ranges 490*a*, 495*a* that include at least one peak frequency for signal gain, and current sample ranges 490*b*, 495*b* that include at least one frequency at which there is no signal gain. The full frequency range $f_{MIN}$ to $f_{MAX}$ may range from 1 Hz to 10 kHz and more preferably from 10 Hz to 1 kHz, and is represented by a horizontal axis having a log scale in graph 400. Partial frequency scan ranges (e.g., $f_1$-$f_2$, $f_3$-$f_5$, $f_4$-$f_6$, $f_7$-$f_8$) corresponding to one or more of these full frequency scan ranges for the current sample ranges 490*a*, 495*a*, 490*b*, 495*b* may be <50%, <20%, <10%, <5%, or <2% of the total plotted frequency scan range on a log scale vs. frequency scale from 5 Hz to 5000 Hz. For example, a sensor could be sampled with a partial frequency scan during a measurement of a sensor, the partial frequency scan comprising less than 20% of the total plotted scanning range on a log scale vs. frequency between 5 Hz and 5000 Hz.

With reference to FIGS. 2A-2C, in some aptamer sensors there is a zero-signal gain frequency. Therefore, a sensor could be sampled only at a voltage that minimizes electrode degradation, such as the voltage position of methylene blue's peak on a gold electrode. For such a sensor, the signal gain may be simply measured at that peak voltage at both a peak signal gain frequency (e.g., associated with current sample ranges 490*a*, 495*a*) vs. a zero signal gain frequency (e.g., the intersection of current sample ranges 490*b*, 495*b*), in order to further minimize electrical degradation of the sensor.

Figure 5A:
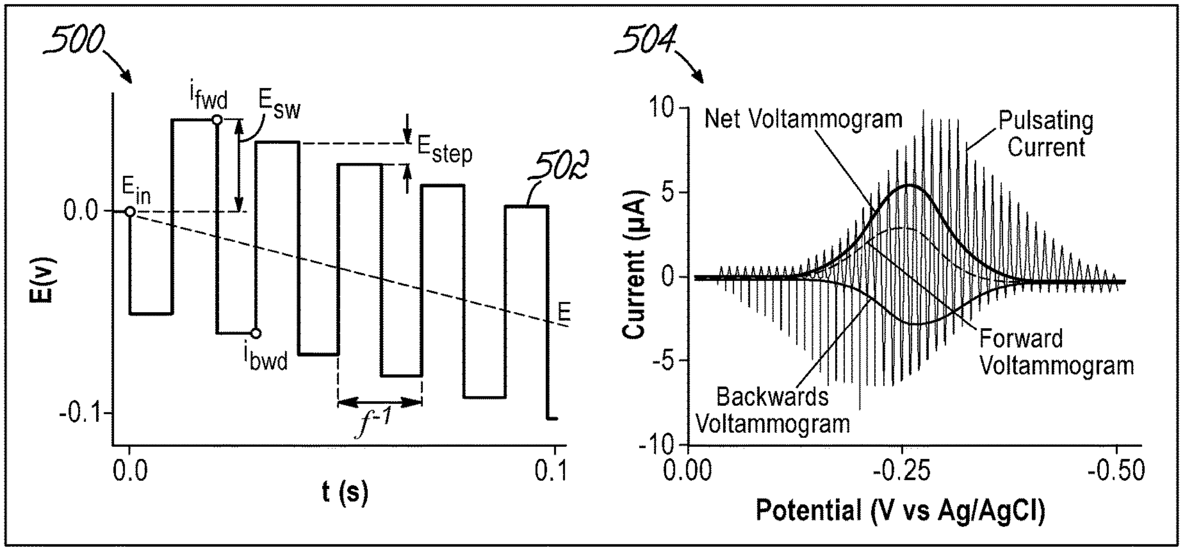
FIGS. 5A and 5B are graphical views illustrating scanning signals that may be provided to a sensor of the sensing devices of FIGS. 1A-1C.

With reference to FIG. 1C, FIG. 5A depicts a graph 500 including a plot 502 of voltage verses time of an electric signal that may be applied between the working electrode 162 and the counter electrode 166 of sensing device 156, and a graph 504 including several plots of current verses voltage, or voltammograms, of a measurement cycle. The current used to generate the plots of graph 504 may be the current flowing between the working electrode 162 and the counter electrode 166, e.g., as measured by current sensor 170. The voltage used to generate the plots of graph 504 may be the voltage between the working electrode 162 and the reference electrode 164, e.g., as measured by voltage sensor 168. The electric signal represented by plot 502 is an example of a SWV signal.

Figure 5B:
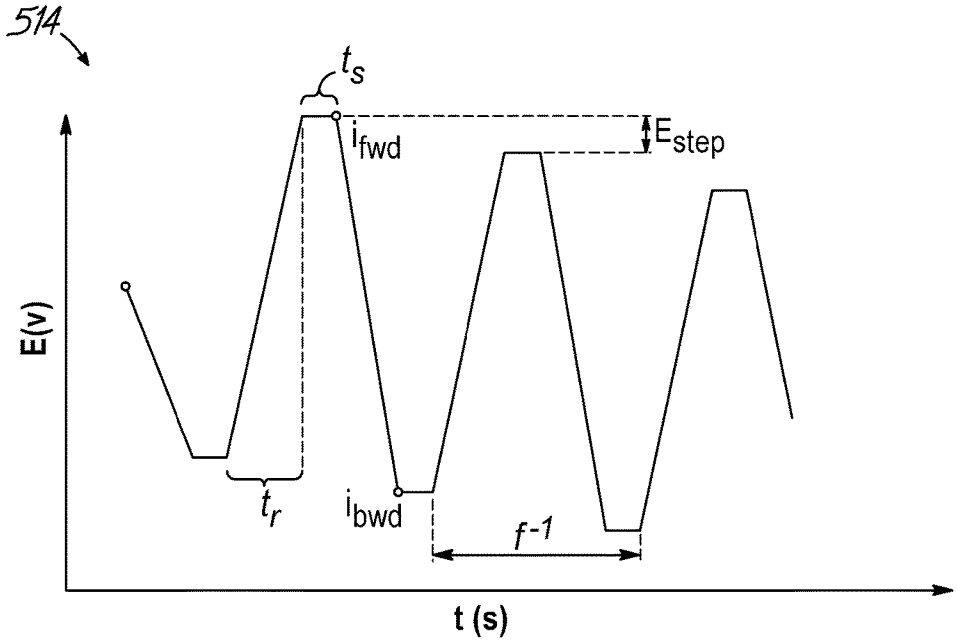

FIG. 5B depicts a graph 514 illustrating a method that reduces the amount of electronic sampling used during device measurement in accordance with an embodiment of the invention. In a square wave voltammetric experiment, the current at a working electrode is measured while the voltage between the working electrode and another electrode (e.g., the counter electrode) is pulsed forward and backward. The voltage waveform can be viewed as a superposition of a regular square wave onto an underlying staircase, as shown by plot 502. In this sense, SWV can be considered a modification of staircase voltammetry.

The current may be sampled at two points during each cycle, e.g., once at the end of the forward voltage pulse ($i_{fwd}$) and again at the end of the reverse voltage pulse ($i_{bwd}$). Thus, each sample is taken immediately before the voltage direction is reversed. As a result of this current sampling technique, the contribution to the current signal resulting from capacitive (sometimes referred to as non-faradaic or charging) current is minimal. As a result of having current sampling at two different instances per square-wave cycle, two current waveforms are collected. Both have diagnostic value, and are therefore preserved. When viewed in isolation, the forward and reverse current waveforms mimic the appearance of a cyclic voltammogram (which corresponds to the anodic or cathodic halves, however, is dependent upon experimental conditions). Despite both the forward and reverse current waveforms having diagnostic worth, it is almost always the case in SWV for the potentiostat software to plot a differential current waveform derived by subtracting the reverse current waveform from the forward current waveform. This differential curve is then plotted against the applied voltage. Peaks in the differential current vs. applied voltage plot are indicative of redox processes, and the magnitudes of the peaks in this plot are used to interpret measurement of the concentration of the analyte in the sample fluid.

With respect to FIG. 5B, a reduced the amount of electronic sampling may be achieved in one or more ways. For example, a lower voltage slew rate (such as provide by a linear ramp) during a ramp phase having a duration $t_r$ may provide the aptamer and blocking monolayer, such as mercaptohexanol, with more time to reorient and reorganize as the applied electric field changes. This additional time may lead to less degradation of the sensor, such as due to detachment of the aptamer or blocking layer or other species that may be absorbed onto the electrode during operation. In addition, the amount of time $t_s$ spent at the peak electric field (or "sampling period") after which current sampling occurs ($i_{fwd}$ or $i_{bwd}$) may be minimized, also reducing strain on the aptamer and blocking monolayer. The sample duration $t_s$ may simply need to be long enough for adequate dissipation of capacitive currents. As non-limiting examples, $t_r$ could be 1, 5, or 9 ms, and $t_s$ could be 0.5, 1, or 3 ms.

Generally, to benefit from this method, the sampling voltage, sampling duration $t_s$, and ramping duration $t_r$ of the ramping period between sampling periods must all be adequately adjusted. The ramp may be linear, sigmoidal, partially sinusoidal, or any other suitable waveform that more gradually ramps to the sampling voltage than a square wave. For a given SWV, frequencies can typically range from several Hz ($t_s+t_r$=n×100 ms) to several kHz ($t_s+t_r$=n×100 μs), and for a given SWV waveform, $t_s$ may be less than or greater than $t_r$. Preferably, to reduce electronic sampling at the sampling voltage, $t_s$ is at least one of less than 90%, 50%, 20%, 10%, 5%, 2%, or 1% of $t_r$. For $t_r$ to enable a more gradual ramp, $t_r$ may more generally be, but is not limited to, greater than 0.2%, 1%, 2%, 5%, 10%, 20%, 50%, 90%, 95% of the quantity $t_r+t_s$. Stated another way, and using the following equation:

$$t_r = \frac{x}{1-x} \times t_s$$

where x is the fraction of each cycle attributed to the ramping duration, $t_r$ may be about 0.2%, 1.0%, 2.0%, 5.3%, 11.1%, 25.0%, 100%, 900%, or 1900% of the sample duration $t_s$. Stated yet another way, and using the following equation:

$$t_s = \frac{1-x}{x} \times t_r$$

where x is the fraction of each cycle attributed to the ramping duration, $t_s$ may be about 49.900%, 9.900%, 4.900%, 1.900%, 900%, 400%, 100%, 11.1%, or 5.3% of the sample duration $t_s$.

EXEMPLARY SCENARIOS

Example 1

An aptamer sensor lacking the features of embodiments of the invention was tested for cortisol. The aptamers were suspended on gold electrodes and protected from nuclease attack by a protecting membrane, chemicals that inhibit nucleases, or non-native base pairs on the aptamer. The aptamer had a redox couple of methylene blue to report current during duty cycles where a range of voltages was probed from 0 to −0.6 volts. The gold electrode contained a blocking layer made of a short, chained passivating species such as 6-Mercapto-1-hexanol to improve the signal to noise of the device. For this device to measure a clinically relevant concentration change without error, three sensors were needed per measurement. Measurements were taken for 2 minutes and the sensor endured 18 hours of operation before its signal degraded to 10% of its original strength, which is a point of complete failure for the device. Two days with a scan every three minutes represents 540 scans in total. This sensor's inability to achieve 24 hour use could be problematic if a user has to apply a sensing device multiple times per day.

Using principles of embodiments of the invention, the scanning voltage can be limited to 10% of the 0.6 volts scanning range, for example, from −0.1 to −0.12 volts for the baseline, −0.29 to −0.31 volts for the peak, −0.4 to −0.42 volts for another baseline, for a total of 0.06 volts of scanning which is 10% of the previous 0.6 volt scan. As a result, the device could provide 5,400 scans instead of merely 540 scans, and potentially up to 180 hours or greater than one week of use. This calculation may further depend on electrode material, surface chemistry and sample fluid conditions, but does illustrate the general impact of embodiments of the invention. The partial voltage scan can comprise one or more voltage scans having a cumulative voltage range that is less than 0.2 volts, less than 0.1 volts, or less than 0.05 volts in voltage scanned. In yet another example, a device with nine sensors, sampled in groups of three, can be measured in a serial fashion to extend the device lifetime by three times.

Example 2

Another application of an embodiment of the inventions may be to reduce the duty cycle as described in FIGS. 2A-2C. Every time a measurement is taken, the controller applies a voltage to the electrode, aptamer, and redox reporter. Over time, this could lead to changes in signal output due to changes in sensor conformation or desorption of the aptamer from the surface. Consider a sample from 0 to −0.6 volts where 6,000 datapoints are taken over six seconds. The reduced duty cycle could scan the same range but only requires 600 datapoints and one second, thereby reducing the charge transfer and sensor active time by a factor of ten.

Testing fluids can vary in chemical makeup between individuals. The sensing device may degrade at differing rates dependent on an individual's sample. As another example, a sensing device in accordance with an embodiment of the invention may use serialized sensors for which a cutoff current measurement is set. Once the current decreases a given amount (e.g., 5%, 10%, or 20%), a sensor may be switched off and a new sensor activated to maintain highly accurate measurements over time given varied sensing environments.

Example 3

A chronoamperometric sensor for the drug tobramycin is presented with a chronoamperometric response from 5E-6 to 1E-6 amps that takes >30 ms for a full chronoamperometric cycle. According to principles disclosed herein, the sensor may instead be measured only from 5E-6 to 2E-6 amps, which takes less than 10 ms, thereby reducing the time of sampling by a factor of three, and improving sensor longevity by as much as three times.

Example 4

Software is used along with electronics to track the peak location on a voltammogram similar to that shown in FIGS. 2A-2D. A baseline can be determined by measuring the slope away from the redox peak, and assigning a threshold for change in slope or curve fit to identify a baseline region. Peak detection is measurable by looking for positive but decreasing in magnitude slope, followed by no slope, followed by negative but increasing in magnitude slope. Software is used along with electronics to track the peak location on a voltammogram similar to that shown in FIGS. 3A and 3B. Such software does not exist with the standard potentiostats dominantly used by researchers of electrochemical aptamer sensors, and to enable peak detection a custom electronics board also may need to be created which is controlled by the software. Such custom electronics and software can be adapted into wearable device formats.

Example 5

In yet another example, a cortisol aptamer sensor with a mercaptohexanol blocking layer was tested on a mechanically roughened gold rod electrode for 70 hours in serum. The duty cycle of the voltage scan for square wave voltammetry was reduced according to principles disclosed herein to 1% of its full scan value. The full scan without reduced sampling would be a square wave voltammogram with 0.035 volt amplitude performed at 400 Hz from 0.5 volts out to 0.45 volts. With reduced sampling the voltage scan was reduced from 0.4 volts to only 0.02 volts (20 times less). The signal was measured out to 70 hours with less than <10% signal loss per day after an initial 4 hour burn-in period. This is a very robust result compared to normal scanning in which the sensor would not last for more than one day.

In general, the routines executed to implement the embodiments of the invention, whether implemented as part of an operating system or a specific application, component, program, object, module or sequence of instructions, or a subset thereof, may be referred to herein as "program code." Program code typically comprises computer-readable instructions that are resident at various times in various memory and storage devices (e.g., non-transitory storage media) in a computer and that, when read and executed by one or more processors in a computer, cause that computer to perform the operations necessary to execute operations or elements embodying the various aspects of the embodiments of the invention. Computer-readable program instructions for carrying out operations of the embodiments of the invention may be, for example, assembly language, source code, or object code written in any combination of one or more programming languages.

The terminology used herein is for the purpose of describing particular embodiments only and is not intended to be limiting of the embodiments of the invention. As used herein, the singular forms "a", "an" and "the" are intended to include both the singular and plural forms, and the terms "and" and "or" are each intended to include both alternative and conjunctive combinations, unless the context clearly indicates otherwise. It will be further understood that the terms "comprises" or "comprising," when used in this specification, specify the presence of stated features, integers, actions, steps, operations, elements, or components, but do not preclude the presence or addition of one or more other features, integers, actions, steps, operations, elements, components, or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A sensing device for measuring an analyte, comprising:

a sensor including a working electrode having a plurality of molecules that reversibly bind to the analyte and a plurality of attached redox tags; and a detection circuit operatively coupled to the sensor and configured to:

perform a full scan of the sensor by applying a first scanning voltage to the sensor, the first scanning voltage including one or both of a forward swept voltage having a first scan range and a backward swept voltage having a second scan range, and perform a partial scan of the sensor by applying a second scanning voltage to the sensor, the second scanning voltage including only a portion of the first scanning voltage that includes a redox peak region and is less than 50% of the full scan.

2. The sensing device of claim 1, wherein the working electrode is one of a plurality of working electrodes configured to measure the analyte, and the detection circuit is configured to perform the partial scan on a different subset of the plurality of working electrodes on each of at least two measurement cycles.

3. The sensing device of claim 2, wherein a plurality of subsets of the working electrodes are scanned, and each subset includes at least three working electrodes that are all scanned as part of a single measurement cycle.

4. The sensing device of claim 2, wherein the plurality of working electrodes includes at least 2, 3, 5, 10, 50, 100, 200, 500, or 1000 electrodes.

5. The sensing device of claim 1, wherein the partial scan is a partial voltage scan, and the detection circuit is further configured to perform a partial frequency scan of the sensor, wherein a full frequency scan of the sensor covers a frequency scan range that includes a full frequency range $f_{MIN}$ to $f_{MAX}$, and the partial frequency scan includes only a portion of the full frequency scan.

6. The sensing device of claim 1, wherein:

the partial scan includes providing a signal having a plurality of sampling periods to the sensor, each sampling period has a sampling duration, at least one set of consecutive sampling periods of the plurality of sampling periods is separated by a ramping period having a ramping duration, and the ramping duration is at least 0.2%, 1.0%, 2.0%, 5.3%, 11.1%, 25.0%, 100%, 900%, or 1900% of the sampling duration.

7. The sensing device of claim 1, wherein the detection circuit is further configured to partially scan the sensor a plurality of times at time intervals that are periodic, non-periodic, or random.

8. The sensing device of claim 1, wherein the partial scan is one of a plurality of partial scans each associated with a measurement cycle, and the portion of the full scan provided by each partial scan varies between measurement cycles.

9. The sensing device of claim 1, wherein the detection circuit is further configured to:

partially scan the sensor a plurality of times, each of the plurality of partial scans being associated with a measurement cycle, and vary the portion of the full scan provided by each partial scan between measurement cycles.

10. The sensing device of claim 1, wherein the detection circuit is further configured to:

partially scan the sensor a plurality of times, each of the plurality of partial scans being associated with a measurement cycle and having at least one of a starting voltage and an ending voltage, and shift at least one of the starting voltage and the ending voltage between measurement cycles.

11. The sensing device of claim 1, wherein the partial scan includes a first portion that generates a baseline sample range, and a second portion that generates a peak sample range.

12. The sensing device of claim 11, wherein the baseline sample range only covers a portion of a baseline region, and the peak sample range only covers a portion of a peak region.

13. The sensing device of claim 12, wherein one or more of the peak region and the baseline region are defined based on a slope of an output generated by the partial scan.

14. The sensing device of claim 11, wherein the full scan has a voltage range of at least 0.4 volts, and the partial scan has a voltage range of no more than 0.2 volts or 0.1 volts.

15. The sensing device of claim 11, wherein the first portion of the partial scan is scanned less frequently than the second portion of the partial scan.

16. The sensing device of claim 15, wherein the second portion of the partial scan is scanned at least two times, five times, 10 times, 50 times, or 100 times as frequently as the first portion of the partial scan.

17. The sensing device of claim 1, wherein the partial scan has a duty cycle that is less than 75%, 50%, 20%, 10%, 5%, 2%, or 1% of the full scan.

18. The sensing device of claim 1, wherein the partial scan generates less than 0.75 times, 0.50 times, 0.20 times, 0.10 times, 0.05 times, 0.02 times, 0.01 times, or 0.001 times the total charge transfer generated by the full scan.

19. The sensing device of claim 1, wherein the partial scan is a partial voltage scan, and the detection circuit is further configured to perform a partial current scan of the sensor, wherein a full current scan of the sensor covers a full current scan range, and the partial current scan includes only a portion of the full current scan.

20. The sensing device of claim 5, wherein the partial frequency scan has a frequency range that is <50%, <20%, <10%, <5%, or <2% of the frequency range of a full frequency scan.

21. A method of measuring an analyte by scanning a sensor that includes a working electrode having a plurality of molecules that reversibly bind to the analyte and a plurality of attached redox tags, comprising:

performing a full scan of the sensor by applying a first scanning voltage to the sensor, the first scanning voltage including one or both of a forward swept voltage having a first scan range and a backward swept voltage having a second scan range, and performing a partial scan of the sensor by applying a second scanning voltage to the sensor, the second scanning voltage including only a portion of the first scanning voltage that includes a redox peak region and is less than 50% of the full scan.

22. The method of claim 21, wherein the working electrode is one of a plurality of working electrodes configured to measure the analyte, and further comprising:

performing the partial scan on a different subset of the plurality of working electrodes on each of at least two measurement cycles.

23. The method of claim 22, wherein a plurality of subsets of the working electrodes are scanned, each subset includes at least three working electrodes, and further comprising:

scanning all of the at least three working electrodes as part of a single measurement cycle.

24. The method of claim 22, wherein the plurality of working electrodes includes at least 2, 3, 5, 10, 50, 100, 200, 500, or 1000 electrodes.

25. The method of claim 21, wherein the partial scan of the sensor is a partial voltage scan, and the method further includes performing a partial frequency scan of the sensor, wherein a full frequency scan of the sensor covers a frequency scan range that includes a full frequency range $f_{MIN}$ to $f_{MAX}$, and the partial frequency scan includes only a portion of the full frequency scan.

26. The method of claim 21, wherein:

partially scanning the sensor includes providing a signal having a plurality of sampling periods to the sensor, each sampling period has a sampling duration, at least one set of consecutive sampling periods of the plurality of sampling periods is separated by a ramping period having a ramping duration, and the ramping duration is at least 0.2%, 1.0%, 2.0%, 5.3%, 11.1%, 25.0%, 100%, 900%, or 1900% of the sampling duration.

27. The method of claim 21, further comprising:

partially scanning the sensor a plurality of times, wherein the partial scans occur at time intervals that are periodic, non-periodic, or random.

28. The method of claim 21, further comprising:

partially scanning the sensor a plurality of times, wherein each of the plurality of partial scans is associated with a measurement cycle, and the portion of the full scan provided by each partial scan varies between measurement cycles.

29. The method of claim 21, wherein the partial scan is a partial voltage scan including one or more portions of a voltage range associated with the full scan.

30. The method of claim 29, wherein the partial voltage scan includes one or more voltage scans that cover a cumulative voltage range of less than 0.2 volts.

31. The method of claim 29, further comprising:

partially scanning the sensor a plurality of times, wherein each of the plurality of partial scans is associated with a measurement cycle, and each partial scan has at least one of a starting voltage and an ending voltage that is shifted in voltage over time between measurement cycles.

32. The method of claim 29, wherein the one or more portions of the voltage range include at least one baseline partial scan of a baseline region, and at least one peak partial scan associated with the full scan.

33. The method of claim 29, further comprising:

partially scanning the sensor a plurality of times to generate a plurality of partial scans, wherein a first portion of the plurality of partial scans includes at least one baseline partial scan, a second portion of the plurality of partial scans includes at least one peak partial scan, and the number of partial scans in the second portion of the plurality of partial scans is greater than the number of partial scans in the first portion of the plurality of partial scans.

34. The method of claim 21, wherein an electrical charge transferred by the partial scan generates less than half of the electrical charge transfer associated with the full scan.

35. The method of claim 21, wherein partially scanning the sensor includes performing a partial voltage scan, and the detection circuit is further configured to perform a partial current scan of the sensor, wherein a full current scan of the sensor covers a full current scan range, and the partial current scan includes only a portion of the full current scan.

36. The method of claim 25, wherein the partial frequency scan includes less than 50% of a full scanning frequency range.

37. The method of claim 36, wherein the partial frequency scan comprises at least one peak frequency for changes in signal gain.

38. The method of claim 36, wherein the partial frequency scan comprises at least one peak frequency with no signal gain.

39. The method of claim 21, wherein partially scanning the sensor includes scanning a first portion of the full scan that generates a baseline sample range, and scanning a second portion of the full scan that generates a peak sample range.

40. The method of claim 39, wherein the baseline sample range only covers a portion of a baseline region, and the peak sample range only covers a portion of a peak region.

41. The method of claim 40, wherein one or more of the peak region and the baseline region are defined based on a slope of an output generated by the partial scan.

42. The method of claim 39, wherein the full scan has a voltage range of at least 0.4 volts, and the partial scan has a voltage range of no more than 0.2 volts or 0.1 volts.

43. The method of claim 39, wherein the first portion of the full scan is scanned less frequently than the second portion of the full scan.

44. The method of claim 43, wherein the second portion of the full scan is scanned at least two times, five times, 10 times, 50 times, or 100 times as frequently as the first portion of the full scan.

45. The method of claim 21, wherein the partial scan has a duty cycle that is less than 75%, 50%, 20%, 10%, 5%, 2%, or 1% of the full scan.

46. The method of claim 21, wherein the partial scan generates less than 0.75 times, 0.50 times, 0.20 times, 0.10 times, 0.05 times, 0.02 times, 0.01 times, or 0.001 times the total charge transfer generated by the full scan.

47. The method of claim 21, wherein the partial scan is a partial voltage scan, and the detection circuit is further configured to perform a partial current scan of the sensor, wherein a full current scan of the sensor covers a full current scan range, and the partial current scan includes only a portion of the full current scan.

48. The method of claim 25, wherein the partial frequency scan has a frequency range that is <50%, <20%, <10%, <5%, or <2% of the frequency range of a full frequency scan.

49. A sensing device for measuring an analyte, comprising:

a sensor including a plurality of working electrodes each having a plurality of molecules that reversibly bind to the analyte and a plurality of attached redox tags; and a detection circuit operatively coupled to the sensor and configured to:

perform a full scan of the sensor by applying a first scanning voltage to the sensor, the first scanning voltage including one or both of a forward swept voltage having a first scan range and a backward swept voltage having a second scan range, and perform a partial scan of the sensor by applying a second scanning voltage to the sensor that includes only a portion of the first scanning voltage that includes a redox peak region and is less than 50% of the full scan, wherein the detection circuit performs one or more of the full scan and the partial scan on a different subset of the plurality of working electrodes on each of at least two consecutive measurement cycles.

50. The sensing device of claim 49, wherein the plurality of working electrodes includes at least 2, 3, 5, 10, 50, 100, 200, 500, or 1000 electrodes.

51. A method of measuring an analyte using a sensor having a plurality of working electrodes each having a plurality of molecules that reversibly bind to the analyte and a plurality of attached redox tags, comprising:

performing a full scan of the sensor by applying a first scanning voltage to the sensor, the first scanning voltage including one or both of a forward swept voltage having a first scan range and a backward swept voltage having a second scan range;

performing a partial scan of the sensor by applying a second scanning voltage to the sensor, the second scanning voltage including only a portion of the first scanning voltage that includes a redox peak region and is less than 50% of the full scan;

scanning a first subset of the working electrodes during a first measurement cycle; and scanning a second subset of the working electrodes during a second measurement cycle that follows the first measurement cycle, wherein the first subset is different from the second subset.

52. The method of claim 51, wherein the plurality of working electrodes includes at least 2, 3, 5, 10, 50, 100, 200, 500, or 1000 electrodes.

* * * * *